(12) United States Patent
Lee et al.

(10) Patent No.: US 8,404,921 B2
(45) Date of Patent: Mar. 26, 2013

(54) WOUND DRESSING

(75) Inventors: Bryony Jayne Lee, Cambridgeshire (GB); Janette Rogers, Cambridgeshire (GB)

(73) Assignee: ConvaTec Technologies, Inc., Las Vegas, NV (US)

( * ) Notice: Subject to any disclaimer, the term of this patent is extended or adjusted under 35 U.S.C. 154(b) by 491 days.

(21) Appl. No.: 12/134,673

(22) Filed: Jun. 6, 2008

(65) Prior Publication Data

US 2009/0177135 A1    Jul. 9, 2009

(30) Foreign Application Priority Data

Jun. 6, 2007  (GB) .................................. 0710846.7

(51) Int. Cl.
  *A61F 15/00* (2006.01)
  *A61F 13/00* (2006.01)
(52) U.S. Cl. .......................................... 602/46; 604/304
(58) Field of Classification Search .............. 602/41–59; 424/443–449; D24/189; 128/888, 889; 604/304–306, 317, 327, 346, 347, 358–382, 604/384, 385.01–385.19, 385.201–385.28
See application file for complete search history.

(56) References Cited

U.S. PATENT DOCUMENTS

| | | | | |
|---|---|---|---|---|
| 3,062,209 A * | 11/1962 | Stowasser | ........................ | 602/48 |
| 4,246,221 A | 1/1981 | McCorsley, III | | |
| 4,360,021 A * | 11/1982 | Stima | ............................ | 604/365 |
| 5,356,372 A | 10/1994 | Donovan et al. | | |
| 5,486,158 A * | 1/1996 | Samuelsen | ...................... | 602/46 |
| 5,505,958 A * | 4/1996 | Bello et al. | ...................... | 424/449 |
| 5,704,905 A * | 1/1998 | Jensen et al. | ..................... | 602/58 |
| 6,834,652 B2 * | 12/2004 | Altman | .......................... | 128/846 |
| 2002/0038099 A1 * | 3/2002 | Griffiths et al. | ................. | 602/54 |
| 2003/0083631 A1 * | 5/2003 | Chen et al. | ...................... | 604/380 |
| 2003/0153860 A1 * | 8/2003 | Nielsen et al. | .................. | 602/43 |
| 2004/0049146 A1 * | 3/2004 | Kolte et al. | ..................... | 602/61 |
| 2004/0162512 A1 * | 8/2004 | Liedtke et al. | .................. | 602/59 |
| 2005/0182347 A1 * | 8/2005 | Bishop et al. | ................... | 602/43 |

FOREIGN PATENT DOCUMENTS

| | | |
|---|---|---|
| EP | 130061 | 8/1988 |
| EP | 092999 | 4/1992 |
| EP | 301874 | 6/1992 |
| EP | 433354 | 1/1994 |
| EP | 476756 | 4/1996 |
| EP | 0941726 | 9/1999 |
| EP | 0768071 | 1/2002 |
| GB | 2375485 | 11/2002 |
| WO | WO93/12275 | 6/1993 |
| WO | WO94/17227 | 8/1994 |
| WO | WO95/14451 | 6/1995 |
| WO | WO 9514451 A1 * | 6/1995 |
| WO | WO00/01425 | 1/2000 |
| WO | WO2007033678 | 3/2007 |
| WO | WO 2007033678 A2 * | 3/2007 |

* cited by examiner

Primary Examiner — Loan Thanh
Assistant Examiner — Tarla Patel
(74) Attorney, Agent, or Firm — Stuart E. Krieger

(57) ABSTRACT

The present invention relates to a wound dressing and in particular a wound dressing for application to the sacrum of a patient. The wound dressing is an absorbent pad having one or more lines about which the dressing can fold.

12 Claims, 2 Drawing Sheets

WOUND DRESSING

BACKGROUND OF THE INVENTION

The present invention relates to a wound dressing and in particular a wound dressing for application to the sacrum of a patient.

Conventional wound dressings are usually planar, rectangular, square or shaped and may be cut into various shapes to enable them to be more easily applied to a body surface.

However, it is sometimes difficult for such dressings to be applied to contoured body areas of a patient, especially if those contours include a deep cleft, without creasing or wrinkling the skin of the patient, the dressing or both. This is particularly the case where the dressing is provided with an adhesive coating over some or all of its body facing surface. Furthermore, even if creasing or wrinkling can be avoided, if the body surface to which the dressing is to be applied is contoured then it can be difficult and time consuming to apply the dressing in an accurate manner over the contours.

European Patent No. 0768071 discloses a dressing especially for sacral wounds in which the dressing is indented with a pattern of lines or grooves in the distal surface of the dressing to form a grid for measuring the wound and also to assist application of the dressing. The indentations make it easier to bend the dressing. There is however a limitation with such dressings in that the dressing must be made from a material in which it is possible to make indentations, for example, a hydrocolloid containing adhesive layer.

For some wounds it is desirable to use alternative materials or additional materials to an adhesive mass in order to tailor the properties of the dressing to the wound and such materials may not allow folding of the dressing in the manner envisaged in the prior art.

For example, it may be desirable to make a wound dressing with a high fluid handling capacity for use as a dressing for highly exudating wounds such as those found on the sacrum. Such a wound dressing may need to be capable of handling, for example, at least 6 g of exudate per 10 cm$^2$ of dressing in 24 hours, and be able to resist appreciable maceration of the skin surrounding the wound and not allow the wound to become desiccated. In the past such dressings included a foam as the absorbent. However, foams are less able to perform, if necessary, when under pressure, such as the weight of the patient, than absorbents which absorb and retain exudate. For such a dressing it may be desirable to use a fibrous absorbent as an additional layer in the dressing. Such a layer needs to be relatively close to the wound in order to function.

SUMMARY OF THE INVENTION

A first aspect the invention provides a wound dressing for use on contoured areas of the body comprising:
an absorbent pad having one or more lines about which the dressing can fold, the absorbent pad being capable of absorbing exudate, and
a flexible adhesive layer on the non-wound contacting side of the absorbent pad.

Such a dressing has the advantage that it can use alternative or additional absorbent materials due to the positioning of the pad and provision of the fold line in the pad.

Preferably, the fold line is a cut which extends partly or wholly through the thickness of the absorbent pad extending from the surface of the pad which faces the wound in use. More preferably, the fold line is a cut which extends wholly through the thickness of the absorbent pad to divide it in two. Where the absorbent pad is divided into two, the pad may be positioned on the adhesive layer so that a gap is left between the two parts of the pad, the gap forming the fold line. Preferably the fold line is straight and located on the central axis of the dressing.

Where the dressing is intended to be applied to the sacral region of a patient, it is preferred that the dressing have a generally triangular, heart or pear shaped outline, but more preferably a square outline with an extending lobe at each corner and preferably that two of the lobes, located on opposite sides of the fold line, are larger than the other two while the dressing is symmetrical about the fold line. This lobed square shape may give a greater surface area for adhesion in those regions where it is difficult to attain adhesion to the skin surrounding the wound in self-adhesive versions of the dressing.

Preferably, the absorbent pad is smaller in area than the adhesive layer so that the pad is surrounded by a margin of adhesive which in use adheres the dressing to the skin surrounding the wound.

The absorbent pad desirably transports wound fluid away from the wound and absorbs exudate while limiting lateral spread. The reduction in lateral spread afforded by a wound dressing of the present invention may reduce maceration of skin surrounding the wound. The absorbency and fluid handling properties of the absorbent pad are preferably not significantly reduced when the dressing is placed under the kinds of pressure usually experienced by wound dressings.

The absorbent pad preferably displays a high absorbency of exudate of at least 10 g/g, preferably 15 g/g to 50 g/g and most preferably an absorbency of from 20 g/g to 50 g/g. Absorbency is measured as described below with reference to the wound contact layer.

Preferably, the lateral wicking of the absorbent core is low, preferably less than 20 mm per minute. Preferably from 1 mm per minute to 15 mm per minute, more preferably from 1 mm per minute to 10 mm per minute.

The absorbent pad is preferably fibrous and most preferably comprises gel forming fibers. The absorbent pad is preferably non-woven. We have found that fibrous layers as opposed to polymeric absorbent layers have the advantage that they are especially able to gel block which resists the lateral spread of exudate. In addition, exudate is absorbed rapidly and retained under pressure.

The fibers suitable for use in the absorbent pad of the present invention include hydrophilic fibers which upon the uptake of wound exudate become moist and slippery or gelatinous and thus reduce the tendency for the surrounding fibers to adhere to the wound. The fibers can be of the type which retain their structural integrity on absorption of exudate or can be of the type which lose their fibrous form and become a structureless gel or a solution on absorption of exudate.

The gel forming fibers are preferably spun sodium carboxymethylcellulose fibers, chemically modified cellulosic fibers, in particular carboxymethylated fibers as described in WO93/12275 to Courtaulds PLC or GB93/01258 to Courtaulds PLC, pectin fibers, alginate fibers and particularly those described in WO 94/17227 to E.R. Squibb and Sons, Inc. or EP433354 to CV Laboratories Ltd. or EP476756 to CV Laboratories Ltd., or composite fibers of alginate and polysaccharide such as those described in EP0892863 to Bristol-Myers Squibb Company, chitosan fibers, hyaluronic acid fibers, or other polysaccharide fibers or fibers derived from gums. The cellulosic fibers preferably have a degree of substitution of at least 0.05 carboxymethyl groups per glucose unit. The production of solvent-spun cellulose fibers is described, for example, in U.S. Pat. Nos. 4,246,221 and 4,196,281 as well as in WO93/12275 mentioned above.

Preferably the gel forming fibers for use in the present invention have an absorbency of either water or saline of at least 15 g/g as measured in the free swell absorbency method, more preferably at least 25 g/g or 50 g/g. The degree of substitution of the gel forming fiber is preferably at least 0.2 carboxymethyl groups per glucose unit, more preferably between 0.3 and 0.5. The tenacity of the fiber is preferably in the range 25-15 cN/tex.

The absorbent pad may, in addition to the gel forming fibers, also comprise other fibers such as textile fibers which can be natural or synthetic but are preferably cellulosic fibers, for example, viscose rayon, multi-limbed viscose, cotton, or regenerated cellulose or fibers having a higher absorbency than most textile fibers such as the multi-limbed cellulose fibers as described in EP301874. In general, textile fibers absorb liquids by capillary action and are not hygroscopic, this means that their absorbencies as measured by the free swell absorbency test are low, such as less than 1 gram of liquid per gram of fiber.

More preferably, the pad comprises an intimate blend of gel forming fibers and cellulosic fibers. Preferably the blend is in the range of up to 25% cellulosic fibers by weight and 75% to 100% gel forming fibers by weight. More preferably, the blend is in the range of up to 50% cellulosic fibers by weight and 50% to 100% gel forming fibers by weight. The blend may be about 50% cellulosic fibers by weight and about 50% gel forming fibers by weight.

The use of a blend of gel forming fibers and cellulosic fibers has the benefit of reducing shrinkage of the dressing when wet, thereby reducing distortion of the dressing which may cause discomfort to the patient. Preferably, shrinkage of the dressing is reduced to less than 25%. If the blend is optimized, shrinkage can be reduced to less than 15%. Shrinkage is measured as the reduction in the surface area of the wound contact layer. It is thought that the structure and composition of the non gelling fibers maintains the shape of the absorbent core of the wound dressing reducing shrinkage of the dressing in use.

The absorption properties of a dressing according to the invention may in use prevent lateral spread of the dressing.

The fibers suitable for use in the present invention can be processed using conventional textile machinery, for example, by the staple route including cutting, carding and needling, and if desired crimping, drafting and spinning.

Preferably the fiber density in the absorbent core is between 150 gm$^2$ and 250 gm$^2$, more preferably the density is approximately 200 gm$^2$.

The dressing may further comprise a flexible wound contact layer which transmits exudate to the absorbent pad.

The wound contact layer is preferably non-adhesive and is configured to transmit exudate to the absorbent pad. Preferably, the wound contact layer creates a moist environment at the wound surface which is conducive to wound healing and reduces the risk of wound desiccation. Furthermore, the absorption properties of the wound contact layer are preferably not significantly compromised under the compression typically applied by the weight of the patient. Where the fold line is a cut in the absorbent pad, the wound contact layer is preferably inserted into the cut to contact the underlying adhesive layer. This gives the advantage that the fold is able to absorb exudate that might otherwise run out of the fold like a channel.

Preferably, the wound contact layer also absorbs exudate from the wound. The wound contact layer preferably has an absorbency of at least 10 g of sodium chloride and calcium chloride solution (BP 1995 Appendix 1A) per gram of absorbent layer measured by the absorbency test for alginate dressings BP 1195. The wound contact layer is preferably fibrous and most preferably comprised of gel forming fibers.

The gel forming fibers are preferably chemically modified cellulosic fibers in the form of a fabric and in particular carboxymethylated cellulose fibers as described in WO00/01425 to Azko Nobel UK Ltd. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method defined above. Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fiber or gel forming fiber. The cellulosic fiber is of known kind and may comprise continuous filament yarn and/or staple fiber. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably, the fabric is hyrdoentangled and thus comprises a series of apertures on a microscopic scale.

Preferably, the dressing further comprises a transmission layer on the non-wound contacting side of the adhesive layer. The transmission layer is preferably a layer having a MVTR of at least 300 gm$^2$/24 hours measured by the method described in 1993 BP Appendix XX J1 or in the range of from 100 gm$^2$/24 hours to 10000 gm$^2$/24 hours. The transmission layer may be in the form of a film/foam laminate, for example, expanded polyurethane foam laminated to a polyurethane film.

Preferably, the transmission layer allows the dressing to be worn whilst the patient bathes or showers without the wound becoming wet.

Preferably, the transmission layer has an outer surface which has a low co-efficient of friction, reducing the risk of sheer, that is, lateral friction causing the wound dressing to sheer, and providing a surface that may be easily wiped clean.

Preferably, the transmission layer is a barrier to bacteria, viruses and external contaminants thereby protecting the wound from infection.

The dressing may also comprise additional optional layers such as a soluble medicated film, for example applied to the contact layer or an odor-absorbing layer such as an activated carbon layer.

The dressing may also comprise a spreading layer. The role of the spreading layer is to laterally spread fluid absorbed by the dressing across the high MVTR transmission layer. This layer may be located on the non-wound facing side of the absorbent pad. The spreading layer may comprise 100% viscose, polyolefin type fibers or a viscose/polyester blends. More preferably the spreading layer is a viscose/polyester hydroentangled non-woven layer.

The spreading layer may be located between the absorbent core and the adhesive layer. An additional keying layer may be positioned between the spreading layer and the absorbent core or the wound contact layer and the absorbent core.

The keying layer may comprise a thin layer of polyamide web. The keying layer may bond the absorbent core to neighboring layers, for example, to the wound contacting layer, the adhesive or the spreading layer, so as to improve the structural integrity of the dressing. This layer may also act in use to reduce the risk of the absorbent layer becoming detached from the dressing when moist. The keying layer may reduce delamination of the dressing in use.

The adhesive layer of the invention serves to hold the absorbent pad in place and may, in a preferred adhesive dressing embodiment, be used to adhere the dressing to the skin. Preferably, the adhesive composition comprises a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatine, guar gum, locust bean gum, karaya gum, and mixtures thereof. The polyisobutylenes may be selected from low molecular weight polyisobutylenes having a viscosity average molecular weight of from 36,000 to 58,000 (Florey). The adhesive layer is capable of absorbing exudate while maintaining adhesion of the dressing.

Alternatively, the adhesive layer may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, an adhesive composition may be prepared having good adhesion to the skin and stretchability. Such compositions and the preparation therefore are disclosed in EP130061.

Preferably, the adhesive is such that the removal of an adhesive wound dressing is not traumatic to the patient. Preferably, the adhesive ensures a secure application of the dressing whist still permitting non-traumatic removal. Non-traumatic dressing removal may be facilitated by using an adhesive which gels slightly upon interaction with a fluid. The gel formation aids dressing removal.

Preferably, the total thickness of the dressing is between 2 mm and 4 mm, more preferably between 2.2 mm and 3.7 mm. This allows the dressing to be more conformable and more discrete in use.

Preferably, a dressing according to the present invention can be worn for at least 7 days, more preferably, the dressing can be worn for 10 or more days. The high fluid handling capacity means that the dressing can be changed less frequently than dressings which are capable of handling less fluid. The less frequently the dressing is changed the more opportunity the wound has to heal.

DETAILED DESCRIPTION OF THE INVENTION

Figure 1:
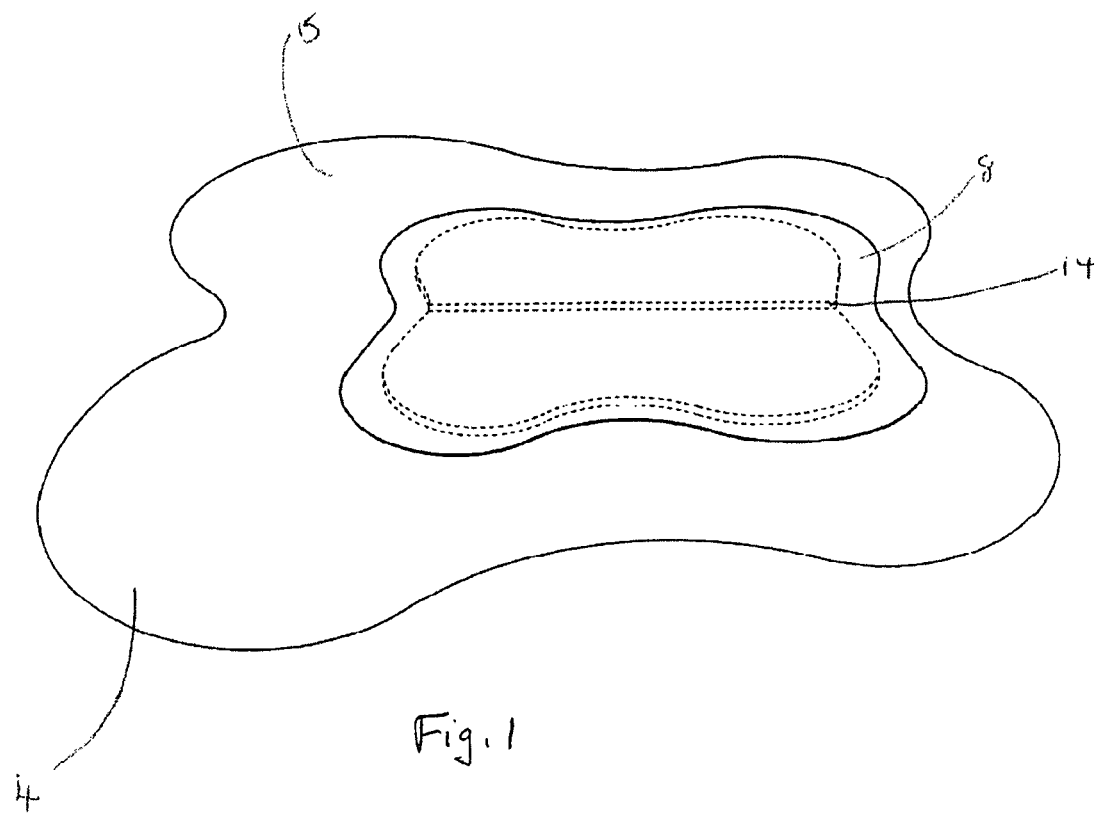
FIG. 1 is a perspective view of the wound contacting surface of a self adherent embodiment of a foldable wound dressing according to the invention.
Figure 2:
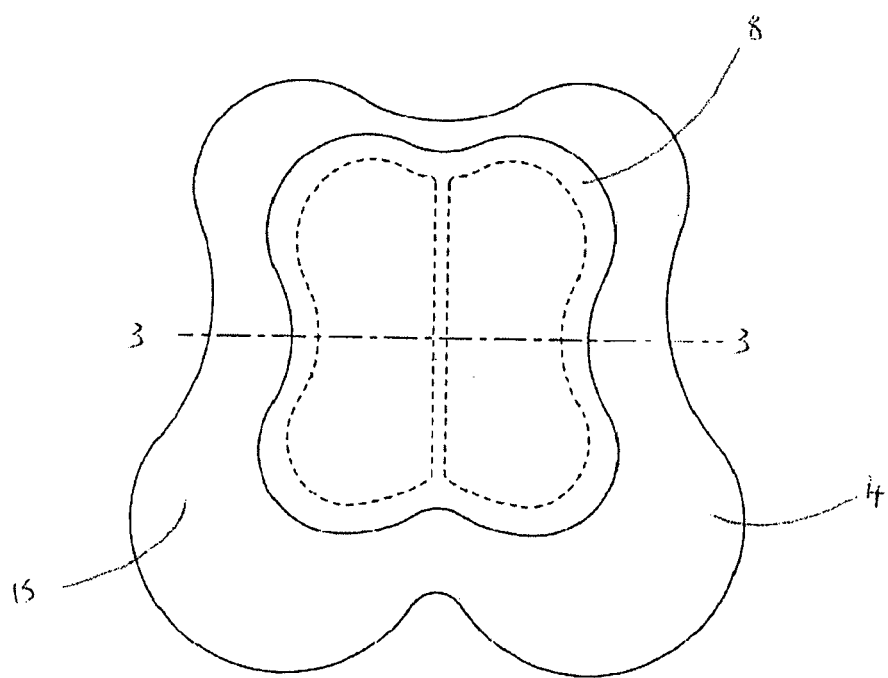
FIG. 2 is a plan view of the dressing of FIG. 1.
Figure 3:
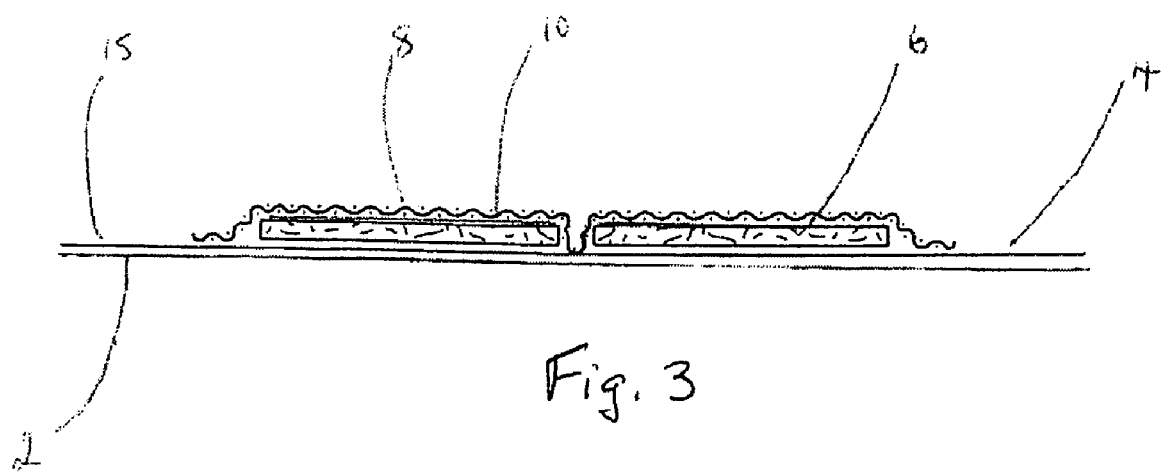
FIG. 3 is a cross-sectional view of the dressing of FIG. 2 taken on the line 3-3.

Referring now to FIGS. 1, 2 and 3, an adhesive multi layered wound dressing according to the invention comprises a transmission layer 2, an adhesive layer 4, an absorbent pad 6 and a wound contacting layer 8.

The wound contacting layer 8 is made from 35 gm$^2$ of a non-woven, hyrdoentangled fabric comprising gel forming fibers.

The absorbent pad is made from 210 gm$^2$ pad of gel forming fibers such as those described in WO93/12275 and sold as the product Hydrocel™ (Acordis). In an alternative embodiment the absorbent pad is a 75/25 blend of Hydrocel™ and Lyocell™. In a yet further embodiment the absorbent pad is a 50/50 blend of Hydrocel™ and Lyocell™.

The adhesive layer 4 is a blend of one or more water soluble hydrocolloids and one or more low molecular weight polyisobutylenes. In an alternative embodiment the adhesive layer may be a polyamide web.

The transmission layer is a polyurethane foam/film laminate.

In the adhesive wound dressing of FIGS. 1, 2 and 3, the absorbent pad 6 is smaller in area than the transmission layer 2 and the adhesive layer 4 and is positioned approximately centrally on the adhesive layer 4. The adhesive holds the absorbent pad 6 in position. The wound contacting layer 8 is larger than the absorbent pad 6 but smaller than the adhesive 4 and transmission layer 2 and is positioned over the absorbent pad 6 in contact with the absorbent pad 6 and the adhesive layer 4. A peripheral rim 15 of the adhesive layer 4 is left exposed and can be used to adhere the dressing to the skin of a patient.

FIG. 3 shows an additional keying layer 10 between the wound contact layer 8 and the absorbent pad 6. The keying layer 10 comprises a polyamide web.

As can best be seen in FIG. 1, the absorbent pad 6 is divided into two parts by fold line 14. Fold line 14 coincides with the central line of symmetry of the dressing. The dressing has a substantially square outline with lobes extending from each corner which give increased adhesive area for adhering the dressing to the wound.

The dressing is placed on a wound, for example a sacral wound by peeling back the release paper from the central area of the dressing and folding the dressing about the fold line 14. The dressing is inserted into the anal cleft and adhered at the margins of the fold line. The release paper is peeled off and the dressing adhered to the wound about its periphery 15.

We claim:

1. A wound dressing for use on contoured areas of the body comprising:
   a gel forming absorbent pad having one or more cut lines extending partly or wholly through a thickness of the absorbent pad from the surface which in use faces the wound the dressing being foldable about the one or more cut lines, the absorbent pad being capable of absorbing exudate; and
   a flexible adhesive layer on a non-wound contacting side of the absorbent pad; and
   wherein the absorbent pad is smaller in area than the adhesive layer so that a peripheral rim of the adhesive layer is left exposed which in use adheres the dressing to the skin surrounding the wound a transmission layer on the non-wound contacting side of the adhesive layer and a keying layer which bonds the absorbent pad to the transmission layer including in between the cut line.

2. The wound dressing as claimed in claim 1, wherein the absorbent pad is positioned on the adhesive layer so that a gap is left between the two parts of the pad, the gap forming the cut line.

3. The wound dressing according to claim 1, wherein the cut line is straight and located on the central axis of the dressing.

4. The wound dressing according to claim 1, wherein the dressing has a generally square outline with an extending lobe at each corner to adapt it to fit the sacrum of a patient.

5. The wound dressing according to claim 4, wherein the lobes, located on opposite sides of the cut line, are larger than the other two while the dressing is symmetrical about the cut line.

6. The wound dressing as claimed in claim 1, wherein the dressing further comprises a flexible wound contact layer which transmits exudate to the absorbent pad.

7. The wound dressing as claimed in claim 1, wherein the dressing is non-self adhesive.

8. The wound dressing according to claim 1, wherein the absorbent pad has an absorbency of exudate of at least 10 g/g.

9. The wound dressing according to claim 1, wherein the absorbent pad is fibrous.

10. The wound dressing according to claim 1, wherein the transmission layer is a foam.

11. The wound dressing according to claim 10, wherein the transmission layer is a polyurethane foam laminated to a polyurethane film.

12. The wound dressing according to claim 1, wherein the keying layer is a polyamide web.

* * * * *